United States Patent
Safai et al.

(10) Patent No.: US 9,927,374 B2
(45) Date of Patent: Mar. 27, 2018

(54) OPTICAL SCANNING ASSEMBLY AND METHOD OF INSPECTING A CHANNEL

(71) Applicant: The Boeing Company, Huntington Beach, CA (US)

(72) Inventors: Morteza Safai, Newcastle, WA (US); Jeffrey G. Thompson, Kent, WA (US)

(73) Assignee: The Boeing Company, Chicago, IL (US)

( * ) Notice: Subject to any disclaimer, the term of this patent is extended or adjusted under 35 U.S.C. 154(b) by 379 days.

(21) Appl. No.: 14/735,908

(22) Filed: Jun. 10, 2015

(65) Prior Publication Data
US 2016/0363437 A1    Dec. 15, 2016

(51) Int. Cl.
*G01B 11/02*   (2006.01)
*G01N 21/954*   (2006.01)
*G01B 11/24*   (2006.01)

(52) U.S. Cl.
CPC ........... *G01N 21/954* (2013.01); *G01B 11/24* (2013.01)

(58) Field of Classification Search
CPC .............................. G01N 21/954; G01B 11/24
See application file for complete search history.

(56) References Cited

U.S. PATENT DOCUMENTS

| | | | |
|---|---|---|---|
| 6,445,939 B1 | 9/2002 | Swanson et al. | |
| 6,564,089 B2 | 5/2003 | Izatt et al. | |
| 7,133,138 B2 | 11/2006 | Horii et al. | |
| 7,366,376 B2 | 4/2008 | Shishkov et al. | |
| 2009/0051938 A1* | 2/2009 | Miousset | G01B 11/245 356/625 |
| 2016/0363437 A1* | 12/2016 | Safai | G01N 21/954 |

OTHER PUBLICATIONS

Wang, Yongqing et al.; Influence of Incident Angle on Distance Detection Accuracy of Point Laser Probe with Charge-Coupled Device: Prediction and Calibration; Optical Engineering; vol. 51(8); Aug. 2012; 7 pp.

* cited by examiner

*Primary Examiner* — Daniel Pihulic
(74) *Attorney, Agent, or Firm* — Armstrong Teasdale LLP

(57) ABSTRACT

An optical scanning assembly for use in inspecting a channel is provided. The assembly includes a housing and an inspection probe that selectively advances from the housing along an axis. The probe includes a light source that directs light towards at least one side wall of the channel and a light detector that receives the light reflected from the side wall. The assembly further includes a controller in communication with the inspection probe. The controller obtains a first optical length measurement for the light reflected from the side wall when the inspection probe is in a first position along the axis within the channel, obtain a second optical length measurement for the light reflected from the side wall when the inspection probe is in a second position along the axis within the channel, and compare the first and second optical length measurements to determine variations in a geometry of the channel.

20 Claims, 4 Drawing Sheets

OPTICAL SCANNING ASSEMBLY AND METHOD OF INSPECTING A CHANNEL

BACKGROUND

The field of the present disclosure relates generally to optical triangulation and, more specifically, to an optical scanning device having a telescoping inspection probe.

At least some known aircraft assemblies implement honeycomb structures in acoustic panels of an engine nacelle for use in attenuating engine noise. Honeycomb structures, also referred to as honeycomb cores, typically include a plurality of hexagonal cells shaped to a desired form. Honeycomb structures are typically manufactured from a thin, flat base material such as metal, paper, and/or composite materials. The flat base material is cut into narrow, elongated strips, which are folded or bent into contoured strips of semi-hexagonal peaks and troughs. For example, an elongated strip of a material may be scored at regularly spaced intervals. To form regular hexagonally shaped cells, the score lines are aligned substantially parallel with the ends of the strip and the material is folded along the score lines to an angle of 60° twice in one direction and then twice in the opposite direction in a continuously alternating sequence. The resulting folded strips are then joined together by adhesive, spot welding, brazing or other known joining methods to form a structure having a series of hexagonally shaped cells, thereby forming a flat honeycomb structure.

The process of forming the honeycomb structure can cause shearing or compression of side walls of the honeycomb structure. Moreover, the side walls can deform during the service life of the acoustic panels. Non-destructive inspection techniques can be used to evaluate the geometry of core cells of the honeycomb structure. However, at least some known non-destructive inspection techniques are unable to accurately quantify an amount of damage or deformation in the core cells.

BRIEF DESCRIPTION

In one aspect, an optical scanning assembly for use in inspecting a channel is provided. The assembly includes a housing and an inspection probe configured to selectively advance from the housing along an axis. The inspection probe includes a light source configured to direct light towards at least one side wall of the channel and a light detector configured to receive the light reflected from the at least one side wall. The assembly further includes a controller in communication with the inspection probe. The controller is configured to obtain a first optical length measurement for the light reflected from the at least one side wall when the inspection probe is in a first position along the axis within the channel, obtain a second optical length measurement for the light reflected from the at least one side wall when the inspection probe is in a second position along the axis within the channel, and compare the first and second optical length measurements to determine variations in a geometry of the channel.

In another aspect, an optical scanning assembly for use in inspecting a structure including a channel is provided. The assembly includes a housing configured to couple to the structure and an inspection probe configured to selectively advance from the housing along an axis. The inspection probe includes a light source configured to direct light towards at least one side wall of the channel and a light detector configured to receive the light reflected from the at least one side wall, such that at least one optical length measurement of the light reflected from the at least one side wall is obtained as the inspection probe advances along the axis.

In yet another aspect, a method of inspecting a channel with an optical scanning assembly including an inspection probe is provided. The inspection probe includes a light source configured to direct light towards at least one side wall of the channel and a light detector configured to receive the light reflected from the at least one side wall. The method includes advancing the inspection probe along an axis extending through the channel, obtaining a first optical length measurement for the light reflected from the at least one side wall when the inspection probe is in a first position along the axis within the channel, obtaining a second optical length measurement for the light reflected from the at least one side wall when the inspection probe is in a second position along the axis within the channel, and comparing the first and second optical length measurements to determine variations in a geometry of the channel.

DETAILED DESCRIPTION

Figure 1:
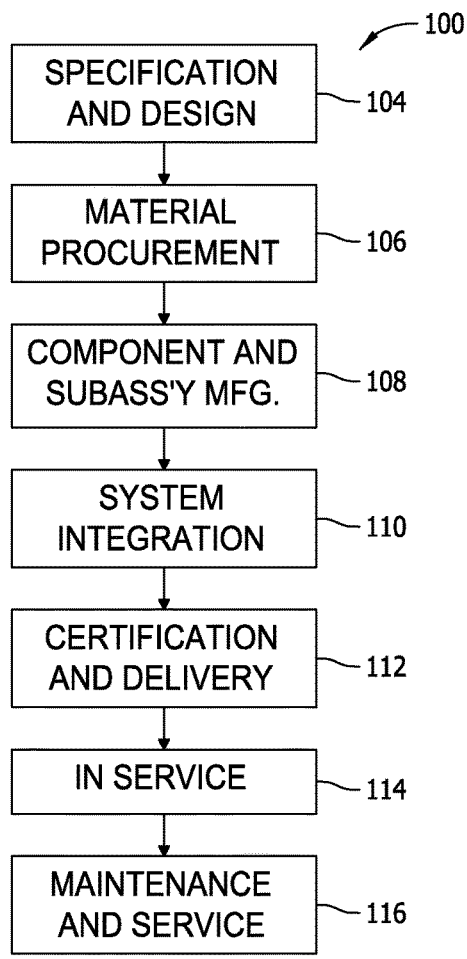
FIG. 1 is a flow diagram of an exemplary aircraft production and service method.

The implementations described herein relate to assemblies and methods for use in inspecting a channel, such as a core cell of a honeycomb structure. The assemblies utilize optical triangulation to determine variations in the geometry of the core cell. More specifically, the optical scanning assembly includes a housing and a telescoping inspection probe that advances along a translation axis while inspecting the core cell. The translation axis extends in a substantially linear direction such that variations in the optical length of a beam of light directed from the inspection probe towards side walls of the core cell are determined when the side walls are deformed, compressed, or otherwise damaged. Moreover, the inspection probe includes one or more micro-opto-electro-mechanical systems to facilitate decreasing the size thereof. As such, the optical scanning assembly described herein is capable of inspecting channels of increasingly small sizes. Moreover, while described in the context of an acoustic panel formed at least partially from a honeycomb structure, it should be understood that the optical scanning assembly can be used to inspect any structure having a channel extending therethrough Referring to the drawings, implementations of the disclosure may be described in the context of an aircraft manufacturing and service method 100 (shown in FIG. 1) and via an aircraft 102 (shown in FIG. 2). During pre-production, including specification and design 104 data of aircraft 102 may be used during the manufacturing process and other materials associated with the airframe may be procured 106. During production, component and subassembly manufacturing 108 and system integration 110 of aircraft 102 occurs, prior to aircraft 102 entering its certification and delivery process 112. Upon successful satisfaction and completion of airframe certification, aircraft 102 may be placed in service 114. While in service by a customer, aircraft 102 is scheduled for periodic, routine, and scheduled maintenance and service 116, including any modification, reconfiguration, and/or refurbishment, for example. In alternative implementations, manufacturing and service method 100 may be implemented via vehicles other than an aircraft.

Each portion and process associated with aircraft manufacturing and/or service 100 may be performed or completed by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

Figure 2:
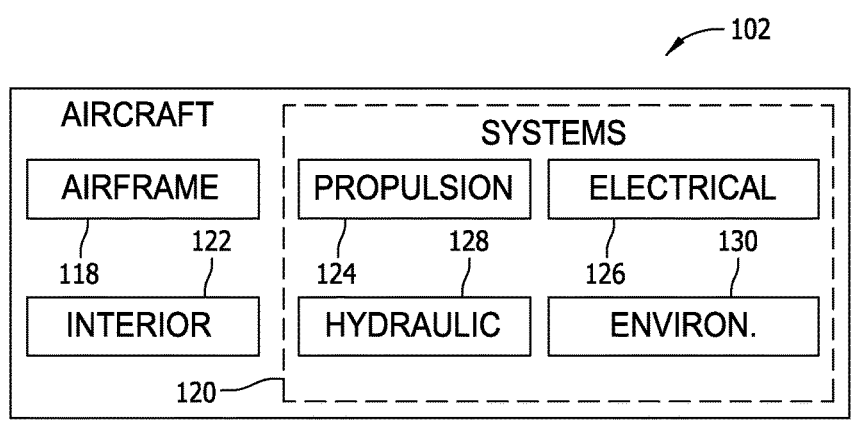
FIG. 2 is a block diagram of an exemplary aircraft.

As shown in FIG. 2, aircraft 102 produced via method 100 may include an airframe 118 having a plurality of systems 120 and an interior 122. Examples of high-level systems 120 include one or more of a propulsion system 124, an electrical system 126, a hydraulic system 128, and/or an environmental system 130. Any number of other systems may be included.

Apparatus and methods embodied herein may be employed during any one or more of the stages of method 100. For example, components or subassemblies corresponding to component production process 108 may be fabricated or manufactured in a manner similar to components or subassemblies produced while aircraft 102 is in service. Also, one or more apparatus implementations, method implementations, or a combination thereof may be utilized during the production stages 108 and 110, for example, by substantially expediting assembly of, and/or reducing the cost of assembly of aircraft 102. Similarly, one or more of apparatus implementations, method implementations, or a combination thereof may be utilized while aircraft 102 is being serviced or maintained, for example, during scheduled maintenance and service 116.

As used herein, the term "aircraft" may include, but is not limited to only including, airplanes, unmanned aerial vehicles (UAVs), gliders, helicopters, and/or any other object that travels through airspace. Further, in an alternative implementation, the aircraft manufacturing and service method described herein may be used in any manufacturing and/or service operation.

Figure 3:
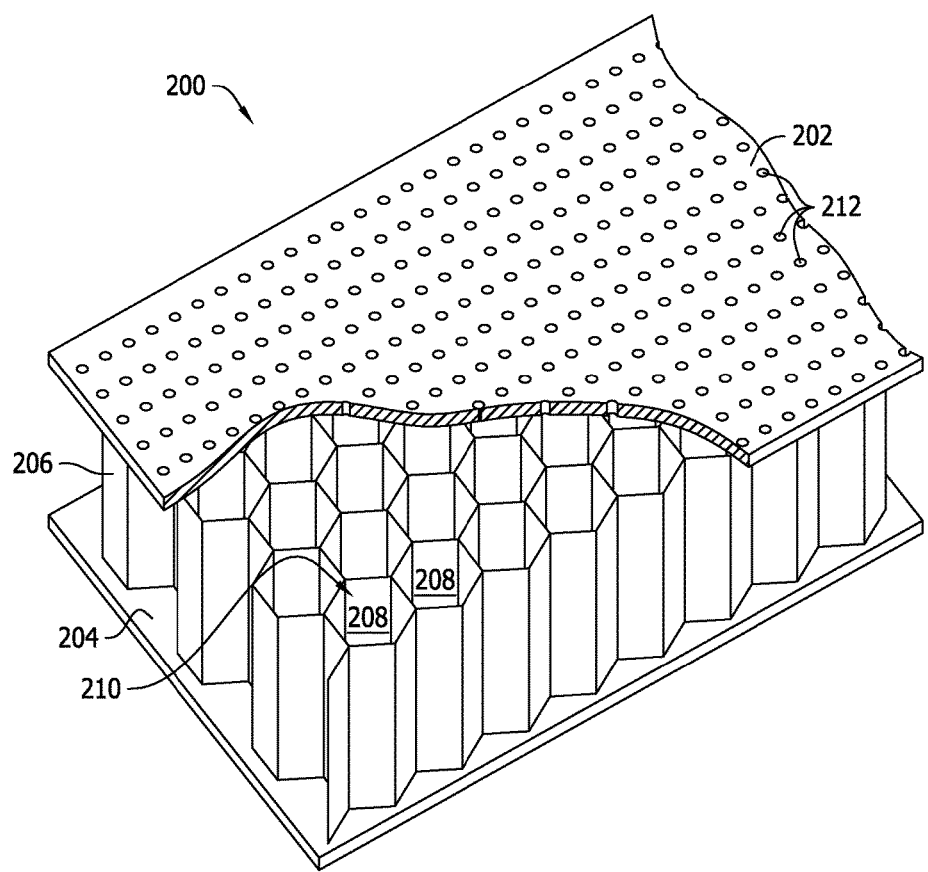
FIG. 3 is a partial cutaway perspective view of an exemplary acoustic liner.

FIG. 3 is a partial cutaway perspective view of an exemplary acoustic liner 200. Acoustic liner 200 includes a perforated face sheet 202, a backing sheet 204, and a honeycomb structure 206 coupled between face sheet 202 and backing sheet 204. Honeycomb structure 206 includes side walls 208 that define a plurality of substantially hexagonal core cells 210. Alternatively, honeycomb structure 206 may be fabricated such that core cells 210 have any cross-sectional shape. Face sheet and backing sheet 202 and 204 are coupled to honeycomb structure 206 in any known manner such as adhesive bonding or welding. Moreover, face sheet 202 includes a plurality of perforations 212 defined therein. Perforations 212 are sized and numbered such that face sheet 202 has a predetermined open area ratio (i.e., the ratio of the open surface area defined by perforations 212 to the total surface area of the face sheet 202).

Figure 4:
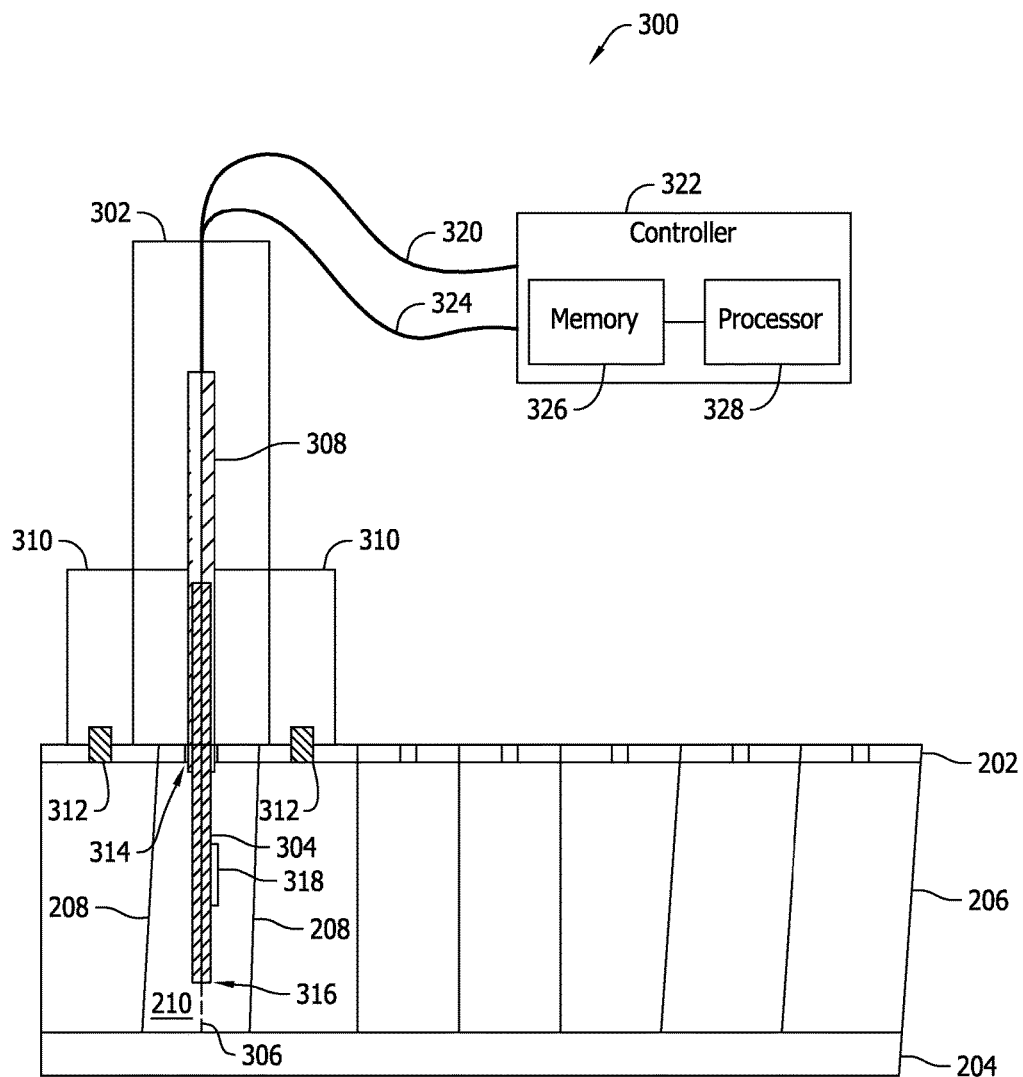
FIG. 4 is a schematic illustration of an exemplary optical scanning assembly that may be used with the acoustic liner shown in FIG. 3.

FIG. 4 is a schematic illustration of an exemplary optical scanning assembly 300 that may be used with acoustic liner 200. In the exemplary implementation, optical scanning assembly 300 includes a housing 302 and an inspection probe 304 that selectively advances from housing 302 along translation axis 306. More specifically, housing 302 includes an internal cavity 308 sized to receive inspection probe 304, and inspection probe 304 selectively advances from internal cavity 308. For example, inspection probe 304 may include an actuating mechanism (not shown) for selectively advancing or retracting inspection probe 304 within internal cavity 308.

In one implementation, housing 302 also includes one or more stabilizing feet 310 coupled thereto. Stabilizing feet 310 include an insertion portion 312 sized to at least partially extend through one of perforations 212 in face sheet 202. Stabilizing feet 310 are positioned about housing 302 to facilitate aligning inspection probe 304 with another perforation 212 in face sheet 202. When insertion portions 312 are coupled within corresponding perforations 212, inspection probe 304 is aligned with another perforation 212 and is capable of selectively advancing through an inlet 314 of a corresponding core cell 210. As such, as will be described in more detail below, stabilizing feet 310 facilitate maintaining inspection probe 304 in a reference position relative to acoustic liner 200 as core cell 210 is inspected. In an alternative implementation, optical scanning assembly 300 does not include stabilizing feet 310, and at least a portion of housing 302 couples to acoustic liner 200 to facilitate maintaining the reference position of inspection probe 304.

In the exemplary implementation, inspection probe 304 includes a light source 316 and a light detector 318. Light source 316 directs light towards at least one side wall 208 of core cell 210, and light detector 318 receives the light reflected from the at least one side wall 208. Moreover, in one implementation, light source 316 and light detector 318 are embodied as micro-opto-electro-mechanical system (MOEMS) type devices. For example, as will be described in more detail below, light source 316 includes a fiber optic cable 320 that channels light therethrough, and one or more micro-optical devices, such as mirrors, microlenses, beam splitters, and collimators. Moreover, light detector 318 may be fabricated from any material that enables optical scanning assembly 300 to function as described herein. Exemplary materials for use in fabricating light detector 318 include, but are not limited to, light-absorbing semiconductor materials such as silicon. As such, implementing MOEMS-type devices in inspection probe 304 enables inspection probe 304 to have a reduced size, such as having a diameter of less than about 0.125 inch.

Optical scanning assembly 300 also includes a controller 322 in communication, either wired or wirelessly, with inspection probe 304. More specifically, in the exemplary implementation, controller 322 is coupled in communication with inspection probe 304 via a control line 324. Controller 322 includes a memory 326 (i.e., a non-transitory computer-readable medium) and a processor 328 coupled to memory 326 for executing programmed instructions. Processor 328 may include one or more processing units (e.g., in a multi-core configuration) and/or include a cryptographic accelerator (not shown). Controller 322 is programmable to perform one or more operations described herein by programming memory 326 and/or processor 328. For example, processor 328 may be programmed by encoding an operation as executable instructions and providing the executable instructions in memory 326.

Processor 328 may include, but is not limited to, a general purpose central processing unit (CPU), a microcontroller, a reduced instruction set computer (RISC) processor, an open media application platform (OMAP), an application specific integrated circuit (ASIC), a programmable logic circuit (PLC), and/or any other circuit or processor capable of executing the functions described herein. The methods described herein may be encoded as executable instructions embodied in a computer-readable medium including, without limitation, a storage device and/or a memory device. Such instructions, when executed by processor 328, cause processor 328 to perform at least a portion of the functions described herein. The above examples are exemplary only, and thus are not intended to limit in any way the definition and/or meaning of the term processor.

Memory 326 is one or more devices that enable information such as executable instructions and/or other data to be stored and retrieved. Memory 326 may include one or more computer-readable media, such as, without limitation, dynamic random access memory (DRAM), synchronous dynamic random access memory (SDRAM), static random access memory (SRAM), a solid state disk, and/or a hard disk. Memory 326 may be configured to store, without limitation, executable instructions, operating systems, applications, resources, installation scripts and/or any other type of data suitable for use with the methods and systems described herein.

Instructions for operating systems and applications are located in a functional form on non-transitory memory 326 for execution by processor 328 to perform one or more of the processes described herein. These instructions in the different implementations may be embodied on different physical or tangible computer-readable media, such as memory 326 or another memory, such as a computer-readable media (not shown), which may include, without limitation, a flash drive and/or thumb drive. Further, instructions may be located in a functional form on non-transitory computer-readable media, which may include, without limitation, smart-media (SM) memory, compact flash (CF) memory, secure digital (SD) memory, memory stick (MS) memory, multimedia card (MMC) memory, embedded-multimedia card (e-MMC), and micro-drive memory. The computer-readable media may be selectively insertable and/or removable from controller 322 to permit access and/or execution by processor 328. In an alternative implementation, the computer-readable media is not removable.

In operation, when inspection probe 304 is aligned with inlet 314 of core cell 210, controller 322 directs inspection probe 304 to advance from housing 302 with the actuating mechanism. Controller 322 then calibrates inspection probe 304 by obtaining a first optical length measurement for the light reflected from the at least one side wall 208 of core cell 210 when inspection probe 304 is in a first position along translation axis 306 within core cell 210. The first position is adjacent to inlet 314 of core cell 210. Moreover, the first optical length measurement is defined as a reference measurement for further optical length measurements to be compared to as inspection probe 304 advances along translation axis 306. Controller 322 then obtains a second optical length measurement for the light reflected from the at least one side wall 208 of core cell 210 when inspection probe 304 is in a second position along translation axis 306 within core cell 210, and compares the first and second optical length measurements to determine variations in the geometry of core cell 210.

As described above, inspection probe 304 advances from housing 302 in a substantially linear direction along translation axis 306. In the exemplary implementation, translation axis 306 extends in a substantially perpendicular direction from face sheet 202. Side walls 208 of core cells 210 likewise extend in a substantially perpendicular direction from face sheet 202 when in an undamaged state. Alternatively, at least a portion of side walls 208 may extend from face sheet 202 in a non-perpendicular direction when in a deformed or compressed state. As such, variations in the geometry of core cell 210 are determined based on variations in the optical length of the light received at light detector 318 as inspection probe 304 advances through core cell 210.

In some implementations, and as will be described in more detail below, controller 322 directs at least a portion of inspection probe 304 to rotate about translation axis 306 within core cell 210 during inspection thereof. As such, inspection probe 304 obtains a plurality of optical length measurements as inspection probe 304 rotates about translation axis 306 to ensure a full scan of core cell 210 is obtained. More specifically, a first set of optical measurements is obtained when inspection probe 304 is at the first position along translation axis 306, and a second set of optical measurements is obtained when inspection probe 304 is at the second position along translation axis 306. An orientation of inspection probe 304 relative to translation axis 306 is determined for each optical length measurement in the first and second sets. Determining the orientation of inspection probe 304 when obtaining optical length measurements facilitates accurately comparing optical length measurements in the first and second sets. As such, in one implementation, controller 322 compares each optical length measurement in the first and second sets obtained at similar inspection probe orientations to determine variations in the geometry of core cell 210.

Controller 322 facilitates directing inspection probe 304 to obtain a full scan of core cell 210 in any manner that enable optical scanning assembly 300 to function as described herein. For example, in one implementation, controller 322 directs inspection probe 304 to obtain optical length measurements continuously as inspection probe 304 advances along translation axis 306 within core cell 210 and rotates about translation axis 306. As such, side walls 208 of core cell 210 are inspected in a substantially helical manner. Alternatively, controller 322 positions inspection probe 304 at predetermined intervals along translation axis 306. Controller 322 then directs inspection probe to perform a 360° scan about translation axis 306 at each predetermined interval, and the results are processed and analyzed by controller 322.

Figure 5:
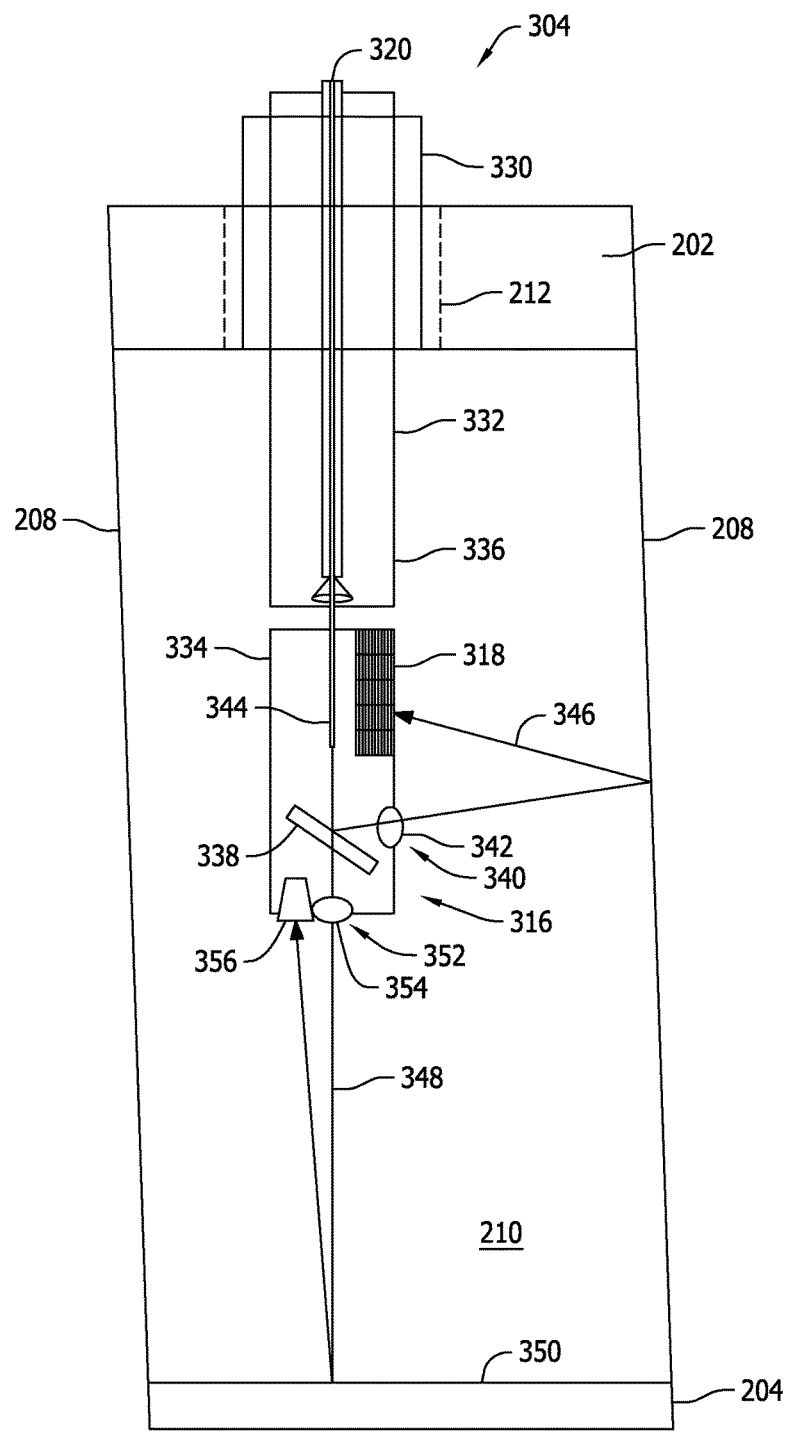
FIG. 5 is a schematic illustration of the inspection probe shown in FIG. 4 at a first axial position within a core cell of the acoustic liner.

FIG. 5 is a schematic illustration of inspection probe 304 within core cell 210 of acoustic liner 200. In the exemplary implementation, housing 302 includes a hollow insertion portion 330 sized to extend at least partially through an opening of a channel, such as through a perforation 212 in face sheet 202. Similar to insertion portions 312 (shown in FIG. 4), hollow insertion portion 330 facilitates maintaining inspection probe 304 in a reference position relative to acoustic liner 200 as core cell 210 is inspected. Moreover hollow insertion portion 330 enables inspection probe 304 to selectively advance and retract therethrough to facilitate inspection of core cell 210.

Inspection probe 304 includes a stationary portion 332 and a rotatable tip portion 334. Rotatable tip portion 334 is coupled to stationary portion 332, and rotates relative to stationary portion 332 about translation axis 306 to facilitate inspecting core cell 210. Moreover, light source 316 includes one or more MOEMS devices that facilitate directing light from rotatable tip portion 334 during inspection of core cell 210. For example, light source 316 includes a collimator 336, a beam splitter 338, and a first light outlet 340 including a first exit lens 342. Collimator 336 facilitates aligning the light channeled through fiber optic cable 320 such that a beam 344 of light is formed. Beam 344 is directed towards beam splitter 338, such that a first portion 346 of beam 344 of light is directed towards the at least one side wall 208 of core cell 210, and such that a second portion 348 of beam 344 of light is directed towards an end wall 350 of core cell 210. More specifically, beam splitter 338 is oriented such that first light outlet 340 channels first portion 346 of beam 344 of light therethrough and towards the at least one side wall 208 of core cell 210.

As described above, the light reflected from the at least one side wall 208 is received at light detector 318. In the exemplary implementation, light detector 318 is coupled to rotatable tip portion 334 and extends only partially about inspection probe 304. At least a portion of light detector 318 is substantially aligned with first light outlet 340 relative to translation axis 306 such that light detector 318 is positioned to receive light reflected from the at least one side wall 208. Alternatively, light detector 318 is coupled to stationary portion 332 and extends about the circumference of inspection probe 304. As such, light detector 318 is positioned to receive light reflected from side walls 208 of core cell 210 as rotatable tip portion 334 rotates about translation axis 306 and first portion 346 of beam 344 of light is directed therefrom.

Moreover, in the exemplary implementation, light source 316 further includes a second light outlet 352 including a second exit lens 354. Beam splitter 338 is oriented such that such that second light outlet 352 channels second portion 348 of beam 344 of light therethrough and towards end wall 350 of core cell 210. Inspection probe 304 further includes a range detector 356 coupled thereto. Range detector 356 is positioned to receive second portion 348 of beam 344 of light reflected from end wall 350. As such, range detector 356 facilitates determining a distance between inspection probe 304 and end wall 350 as inspection probe 304 advances along translation axis 306 to ensure a safe distance is maintained therebetween, and to ensure a full scan of core cell 210 is conducted.

A method of inspecting a channel, such as core cell 210, with optical scanning assembly 300. The method includes advancing inspection probe 304 along translation axis 306 extending through the channel. The method also includes obtaining a first optical length measurement for the light reflected from at least one side wall 208 when inspection probe 304 is in a first position along translation axis 306 within the channel, and obtaining a second optical length measurement for the light reflected from the at least one side wall 208 when inspection probe 304 is in a second position along translation axis 306 within the channel. The method further includes comparing the first and second optical length measurements to determine variations in the geometry of the channel.

In one implementation, the method further includes selecting the first optical length measurement as a reference measurement for comparison to further optical length measurements. The method also includes rotating inspection probe 304 about translation axis 306 such that a first set of optical length measurements is obtained when inspection probe 304 is at the first positioned along translation axis 306, and such that a second set of optical length measurements is obtained when inspection probe 304 is at the second position along translation axis 306. In one implementation, the second set of optical length measurements is obtained continuously as inspection probe 304 advances along translation axis 306 and rotates about translation axis 306. Alternatively, a plurality of sets of optical length measurements are obtained as inspection probe 304 is positioned at predetermined intervals along translation axis 306.

This written description uses examples to disclose various implementations, including the best mode, and also to enable any person skilled in the art to practice the various implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An optical scanning assembly for use in inspecting a channel, said assembly comprising:
   a housing comprising a hollow insertion portion configured to maintain said housing in a reference position when inspecting the channel;
   an inspection probe configured to selectively advance through said hollow insertion portion and into the channel along an axis, wherein said inspection probe comprises a light source configured to direct light towards at least one side wall of the channel and a light detector configured to receive the light reflected from the at least one side wall; and
   a controller in communication with said inspection probe, said controller configured to:
      obtain a first optical length measurement for the light reflected from the at least one side wall when the inspection probe is in a first position along the axis within the channel;
      obtain a second optical length measurement for the light reflected from the at least one side wall when the inspection probe is in a second position along the axis within the channel; and
      compare the first and second optical length measurements to determine variations in a geometry of the channel.

2. The assembly in accordance with claim 1, wherein said inspection probe is configured to rotate about the axis, said controller further configured to:
   obtain a plurality of optical length measurements as the inspection probe rotates about the axis such that a first set of optical length measurements is obtained when the inspection probe is at the first position along the axis, and such that a second set of optical length measurements is obtained when the inspection probe is at the second position along the axis.

3. The assembly in accordance with claim 1, wherein said inspection probe comprises a beam splitter positioned such that a first portion of the light is directed towards the at least one side wall of the channel, and such that a second portion of the light is directed towards an end wall of the channel.

4. The assembly in accordance with claim 3 further comprising a range detector coupled to said inspection probe, wherein said range detector is positioned to receive the second portion of the light reflected from the end wall.

5. The assembly in accordance with claim 1, wherein said inspection probe comprises a stationary portion and a rotatable tip portion configured to rotate relative to said stationary portion, said light source configured to direct the light from said rotatable tip portion.

6. The assembly in accordance with claim 1, wherein said light source comprises a light outlet configured to channel the light therethrough and towards the at least one side wall of the channel, said light outlet substantially aligned with said light detector relative to the axis.

7. The assembly in accordance with claim 1, wherein said light source comprises a fiber optic cable configured to channel the light therethrough.

8. The assembly in accordance with claim 1, wherein said light source and said light detector comprise at least one micro-opto-electro-mechanical system.

9. An optical scanning assembly for use in inspecting a structure including a channel, said assembly comprising:
 a housing configured to couple to the structure, said housing comprising a hollow insertion portion configured to maintain said housing in a reference position when inspecting the channel; and
 an inspection probe configured to selectively advance through said hollow insertion portion and into the channel along an axis, wherein said inspection probe comprises a light source configured to direct light towards at least one side wall of the channel and a light detector configured to receive the light reflected from the at least one side wall, such that at least one optical length measurement of the light reflected from the at least one side wall is obtained as said inspection probe advances along the axis.

10. The assembly in accordance with claim 9 further comprising at least one stabilizing foot coupled to said housing, said at least one stabilizing foot configured to couple to the structure to substantially maintain said inspection probe in a reference position.

11. The assembly in accordance with claim 9, wherein said hollow insertion portion is sized to extend at least partially through an opening in the channel.

12. The assembly in accordance with claim 9, wherein said inspection probe comprises a stationary portion and a rotatable tip portion configured to rotate relative to said stationary portion, said light source configured to direct the light from said rotatable tip portion.

13. The assembly in accordance with claim 9, wherein said light source comprises a light outlet configured to channel the light therethrough and towards the at least one side wall of the channel, said light outlet substantially aligned with said light detector relative to the axis.

14. The assembly in accordance with claim 9, wherein said light source comprises a fiber optic cable configured to channel the light therethrough.

15. The assembly in accordance with claim 9, wherein said light source and said light detector comprise at least one micro-opto-electro-mechanical system.

16. A method of inspecting a channel with an optical scanning assembly including a housing and an inspection probe, the channel accessible through a perforation in the face sheet, the inspection probe including a light source configured to direct light towards at least one side wall of the channel and a light detector configured to receive the light reflected from the at least one side wall, said method comprising:
 positioning a hollow insertion portion of the housing within the perforation in the face sheet such that the housing is maintained in a reference position relative to the face sheet;
 advancing the inspection probe through the hollow insertion portion and into the channel along an axis that extends through the channel;
 obtaining a first optical length measurement for the light reflected from the at least one side wall when the inspection probe is in a first position along the axis within the channel;
 obtaining a second optical length measurement for the light reflected from the at least one side wall when the inspection probe is in a second position along the axis within the channel; and
 comparing the first and second optical length measurements to determine variations in a geometry of the channel.

17. The method in accordance with claim 16 further comprising selecting the first optical length measurement as a reference measurement for comparison to further optical length measurements.

18. The method in accordance with claim 16 further comprising rotating the inspection probe about the axis such that a first set of optical length measurements is obtained when the inspection probe is at the first position along the axis, and such that a second set of optical length measurements is obtained when the inspection probe is at the second position along the axis.

19. The method in accordance with claim 18 further comprising obtaining the second set of optical length measurements continuously as the inspection probe advances along the axis and rotates about the axis.

20. The method in accordance with claim 18 further comprising obtaining a plurality of sets of optical length measurements as the inspection probe is positioned at predetermined intervals along the axis.

* * * * *